United States Patent
Roberts

(10) Patent No.: US 8,055,350 B2
(45) Date of Patent: Nov. 8, 2011

(54) SYSTEM AND METHOD FOR ENABLING COMMUNICATIONS WITH IMPLANTABLE MEDICAL DEVICES

(75) Inventor: Earle Roberts, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 88 days.

(21) Appl. No.: 12/691,364

(22) Filed: Jan. 21, 2010

(65) Prior Publication Data

US 2010/0121414 A1    May 13, 2010

Related U.S. Application Data

(62) Division of application No. 11/116,108, filed on Apr. 27, 2005, now Pat. No. 7,664,553.

(51) Int. Cl.
*A61N 1/00* (2006.01)

(52) U.S. Cl. .............. 607/60; 607/30; 607/32

(58) Field of Classification Search .......... 607/30, 607/32, 60

See application file for complete search history.

(56) References Cited

U.S. PATENT DOCUMENTS

| | | |
|---|---|---|
| 3,914,586 A | 10/1975 | McIntosh |
| 4,341,982 A | 7/1982 | Lahti et al. |
| 4,404,972 A | 9/1983 | Gordon et al. |
| 4,441,498 A | 4/1984 | Nordling |
| 4,486,739 A | 12/1984 | Franaszek et al. |
| 4,519,401 A | 5/1985 | Ko et al. |
| 4,542,535 A | 9/1985 | Bates et al. |
| 4,543,954 A | 10/1985 | Cook et al. |
| 4,562,841 A | 1/1986 | Brockway et al. |
| 4,731,814 A | 3/1988 | Becker et al. |
| 4,799,059 A | 1/1989 | Grindahl et al. |
| 4,944,299 A | 7/1990 | Silvian |
| 4,945,909 A | 8/1990 | Fearnot et al. |
| 5,025,808 A | 6/1991 | Hafner |
| 5,113,869 A | 5/1992 | Nappholz et al. |
| 5,171,977 A | 12/1992 | Morrison |
| 5,230,003 A | 7/1993 | Dent et al. |
| 5,287,384 A | 2/1994 | Avery et al. |
| 5,292,343 A | 3/1994 | Blanchette et al. |

(Continued)

FOREIGN PATENT DOCUMENTS

EP    1308184 A2    5/2003

(Continued)

OTHER PUBLICATIONS

"U.S. Appl. No. 11/733,339, Interview Summary mailed Aug. 13, 2009", 2 pgs.

(Continued)

*Primary Examiner* — Niketa Patel
*Assistant Examiner* — Nicole F Lavert
(74) *Attorney, Agent, or Firm* — Schwegman, Lundberg & Woessner, P.A.

(57) ABSTRACT

A method is presented for enabling radio-frequency (RF) communications between an implantable medical device and an external device in a manner which reduces the power requirements of the implantable device by duty cycling its RF circuitry. A wakeup scheme for the implantable device is provided in which the external device transmits a data segment containing a repeating sequence of special wakeup characters and a device ID in order to establish a communications session with the implantable device. The wakeup scheme may be designed to operate using multiple communications channels.

20 Claims, 3 Drawing Sheets

U.S. PATENT DOCUMENTS

| | | |
|---|---|---|
| 5,300,093 A | 4/1994 | Koestner et al. |
| 5,314,453 A | 5/1994 | Jeutter |
| 5,342,408 A | 8/1994 | deCoriolis et al. |
| 5,350,411 A | 9/1994 | Ryan et al. |
| 5,350,412 A | 9/1994 | Hoegnelid et al. |
| 5,370,666 A | 12/1994 | Lindberg et al. |
| 5,394,433 A | 2/1995 | Bantz et al. |
| 5,476,488 A | 12/1995 | Morgan et al. |
| 5,486,200 A | 1/1996 | Lindemans |
| 5,532,708 A | 7/1996 | Krenz et al. |
| 5,562,713 A | 10/1996 | Silvian |
| 5,568,510 A | 10/1996 | Tam |
| 5,579,876 A | 12/1996 | Adrian et al. |
| 5,593,430 A | 1/1997 | Renger |
| 5,617,871 A | 4/1997 | Burrows |
| 5,630,835 A | 5/1997 | Brownlee |
| 5,650,759 A | 7/1997 | Hittman et al. |
| 5,683,432 A | 11/1997 | Goedeke et al. |
| 5,694,952 A | 12/1997 | Lidman et al. |
| 5,697,958 A | 12/1997 | Paul et al. |
| 5,725,559 A | 3/1998 | Alt et al. |
| 5,729,680 A | 3/1998 | Belanger et al. |
| 5,752,976 A | 5/1998 | Duffin et al. |
| 5,752,977 A | 5/1998 | Grevious et al. |
| 5,766,232 A | 6/1998 | Grevious et al. |
| 5,807,397 A | 9/1998 | Barreras |
| 5,843,139 A | 12/1998 | Goedeke et al. |
| 5,861,019 A | 1/1999 | Sun et al. |
| 5,870,391 A | 2/1999 | Nago |
| 5,881,101 A | 3/1999 | Furman et al. |
| 5,887,022 A | 3/1999 | Lee |
| 5,895,485 A | 4/1999 | Loechel et al. |
| 5,940,384 A | 8/1999 | Carney et al. |
| 6,009,350 A | 12/1999 | Renken |
| 6,031,863 A | 2/2000 | Jusa et al. |
| 6,044,485 A | 3/2000 | Dent et al. |
| 6,088,381 A | 7/2000 | Myers, Jr. |
| 6,093,146 A | 7/2000 | Filangeri |
| 6,115,583 A | 9/2000 | Brummer et al. |
| 6,115,634 A | 9/2000 | Donders et al. |
| 6,115,636 A | 9/2000 | Ryan |
| 6,130,905 A | 10/2000 | Wakayama |
| 6,155,208 A | 12/2000 | Schell et al. |
| 6,167,310 A | 12/2000 | Grevious |
| 6,167,312 A | 12/2000 | Goedeke |
| 6,169,925 B1 | 1/2001 | Villaseca et al. |
| 6,219,580 B1 | 4/2001 | Faltys et al. |
| 6,223,083 B1 | 4/2001 | Rosar |
| 6,240,317 B1 | 5/2001 | Villaseca et al. |
| 6,263,246 B1 | 7/2001 | Goedeke et al. |
| 6,336,900 B1 | 1/2002 | Alleckson et al. |
| 6,336,903 B1 | 1/2002 | Bardy |
| 6,381,492 B1 | 4/2002 | Rockwell et al. |
| 6,385,318 B1 | 5/2002 | Oishi |
| 6,388,628 B1 | 5/2002 | Dettloff et al. |
| 6,416,471 B1 | 7/2002 | Kumar et al. |
| 6,424,867 B1 | 7/2002 | Snell et al. |
| 6,427,088 B1 | 7/2002 | Bowman, IV et al. |
| 6,434,429 B1 | 8/2002 | Kraus et al. |
| 6,443,891 B1 | 9/2002 | Grevious |
| 6,456,256 B1 | 9/2002 | Amundson et al. |
| 6,456,875 B1 | 9/2002 | Wilkinson et al. |
| 6,463,329 B1 | 10/2002 | Goedeke |
| 6,470,215 B1 | 10/2002 | Kraus et al. |
| 6,471,645 B1 | 10/2002 | Warkentin |
| 6,472,991 B1 * | 10/2002 | Schulman et al. ......... 340/995.1 |
| 6,482,154 B1 | 11/2002 | Haubrich et al. |
| 6,490,487 B1 | 12/2002 | Kraus et al. |
| 6,505,072 B1 | 1/2003 | Linder et al. |
| 6,527,729 B1 | 3/2003 | Turcott |
| 6,531,982 B1 | 3/2003 | White et al. |
| 6,535,763 B1 | 3/2003 | Hiebert et al. |
| 6,535,766 B1 | 3/2003 | Thompson et al. |
| 6,562,000 B2 | 5/2003 | Thompson et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,574,503 B2 | 6/2003 | Ferek-Petric |
| 6,574,509 B1 | 6/2003 | Kraus et al. |
| 6,574,510 B2 | 6/2003 | Von Arx et al. |
| 6,585,644 B2 | 7/2003 | Lebel et al. |
| 6,600,952 B1 | 7/2003 | Snell et al. |
| 6,602,191 B2 | 8/2003 | Quy |
| 6,622,043 B1 | 9/2003 | Kraus et al. |
| 6,622,050 B2 | 9/2003 | Thompson |
| 6,631,296 B1 | 10/2003 | Parramon et al. |
| 6,648,821 B2 | 11/2003 | Lebel et al. |
| 6,659,948 B2 | 12/2003 | Lebel et al. |
| 6,675,045 B2 | 1/2004 | Mass et al. |
| 6,687,546 B2 | 2/2004 | Lebel et al. |
| 6,763,269 B2 | 7/2004 | Cox |
| 6,768,730 B1 | 7/2004 | Whitehill |
| 6,801,807 B2 | 10/2004 | Abrahamson |
| 6,804,559 B1 | 10/2004 | Kraus et al. |
| 6,809,701 B2 | 10/2004 | Amundson et al. |
| 6,868,288 B2 | 3/2005 | Thompson |
| 6,897,788 B2 | 5/2005 | Khair et al. |
| 6,970,735 B2 | 11/2005 | Uber, III et al. |
| 6,978,181 B1 | 12/2005 | Snell |
| 6,985,773 B2 | 1/2006 | Von Arx et al. |
| 6,993,393 B2 | 1/2006 | Von Arx et al. |
| 7,013,178 B2 | 3/2006 | Reinke et al. |
| 7,069,086 B2 | 6/2006 | Von Arx |
| 7,110,823 B2 | 9/2006 | Whitehurst et al. |
| 7,155,290 B2 | 12/2006 | Von et al. |
| 7,177,700 B1 | 2/2007 | Cox |
| 7,218,969 B2 | 5/2007 | Vallapureddy et al. |
| 7,274,642 B2 | 9/2007 | Sako et al. |
| 7,280,872 B1 | 10/2007 | Mosesov et al. |
| 7,289,853 B1 | 10/2007 | Campbell et al. |
| 7,319,903 B2 | 1/2008 | Bange et al. |
| 7,324,012 B2 | 1/2008 | Mann et al. |
| 7,359,753 B2 | 4/2008 | Bange et al. |
| 7,519,430 B2 | 4/2009 | Arx et al. |
| 7,539,489 B1 * | 5/2009 | Alexander ................ 455/423 |
| 7,573,422 B2 | 8/2009 | Harvey et al. |
| 7,623,922 B2 | 11/2009 | Bange et al. |
| 7,787,953 B2 | 8/2010 | Vallapureddy et al. |
| 2001/0012955 A1 | 8/2001 | Goedeke et al. |
| 2001/0047125 A1 | 11/2001 | Quy |
| 2002/0019606 A1 | 2/2002 | Lebel et al. |
| 2002/0046276 A1 | 4/2002 | Coffey et al. |
| 2002/0049480 A1 | 4/2002 | Lebel et al. |
| 2002/0065509 A1 | 5/2002 | Lebel et al. |
| 2002/0065539 A1 | 5/2002 | Von Arx et al. |
| 2002/0065540 A1 | 5/2002 | Lebel et al. |
| 2002/0109621 A1 | 8/2002 | Khair et al. |
| 2002/0115912 A1 | 8/2002 | Muraki et al. |
| 2002/0123672 A1 | 9/2002 | Christophersom et al. |
| 2002/0143372 A1 | 10/2002 | Snell et al. |
| 2002/0147388 A1 | 10/2002 | Mass et al. |
| 2002/0183806 A1 | 12/2002 | Abrahamson et al. |
| 2003/0028902 A1 | 2/2003 | Cubley et al. |
| 2003/0050535 A1 | 3/2003 | Bowman, IV et al. |
| 2003/0083719 A1 | 5/2003 | Shankar et al. |
| 2003/0097157 A1 | 5/2003 | Wohlgemuth et al. |
| 2003/0114891 A1 | 6/2003 | Hiebert et al. |
| 2003/0114897 A1 * | 6/2003 | Von Arx et al. ................ 607/60 |
| 2003/0114898 A1 | 6/2003 | Von Arx et al. |
| 2003/0146835 A1 | 8/2003 | Carter |
| 2003/0149459 A1 | 8/2003 | Von Arx et al. |
| 2003/0187484 A1 | 10/2003 | Davis et al. |
| 2003/0216793 A1 | 11/2003 | Karlsson et al. |
| 2003/0220673 A1 | 11/2003 | Snell |
| 2004/0030260 A1 | 2/2004 | Von Arx |
| 2004/0047434 A1 | 3/2004 | Waltho |
| 2004/0102815 A1 | 5/2004 | Balczewski et al. |
| 2004/0127959 A1 | 7/2004 | Amundson et al. |
| 2004/0167587 A1 | 8/2004 | Thompson |
| 2004/0176811 A1 | 9/2004 | Von Arx et al. |
| 2004/0176822 A1 | 9/2004 | Thompson et al. |
| 2004/0260363 A1 | 12/2004 | Arx et al. |
| 2005/0204134 A1 | 9/2005 | Von Arx et al. |
| 2005/0222933 A1 | 10/2005 | Wesby |
| 2005/0240245 A1 | 10/2005 | Bange et al. |
| 2005/0245992 A1 | 11/2005 | Persen et al. |
| 2005/0283208 A1 | 12/2005 | Von Arx et al. |

| | | |
|---|---|---|
| 2005/0283209 A1 | 12/2005 | Katoozi et al. |
| 2005/0288738 A1 | 12/2005 | Bange et al. |
| 2006/0025834 A1 | 2/2006 | Von Arx et al. |
| 2006/0029100 A1 | 2/2006 | Dove |
| 2006/0030901 A1 | 2/2006 | Quiles et al. |
| 2006/0030902 A1 | 2/2006 | Quiles et al. |
| 2006/0030903 A1 | 2/2006 | Seeberger et al. |
| 2006/0030904 A1 | 2/2006 | Quiles |
| 2006/0071756 A1 | 4/2006 | Steeves |
| 2006/0116744 A1 | 6/2006 | Von Arx et al. |
| 2006/0161222 A1 | 7/2006 | Haubrich et al. |
| 2006/0161223 A1 | 7/2006 | Vallapureddy et al. |
| 2006/0195161 A1 | 8/2006 | Li |
| 2006/0195162 A1 | 8/2006 | Arx et al. |
| 2006/0247736 A1 | 11/2006 | Roberts |
| 2007/0049983 A1 | 3/2007 | Freeberg |
| 2007/0100396 A1 | 5/2007 | Freeberg |
| 2007/0185550 A1 | 8/2007 | Vallapureddy et al. |
| 2008/0015655 A1 | 1/2008 | Bange et al. |
| 2008/0015656 A1 | 1/2008 | Bange et al. |
| 2008/0114412 A1 | 5/2008 | Bange et al. |
| 2008/0215121 A1 | 9/2008 | Bange et al. |

FOREIGN PATENT DOCUMENTS

| | | |
|---|---|---|
| EP | 1495783 A1 | 1/2005 |
| WO | WO-9500202 A1 | 1/1995 |
| WO | WO-9819400 A1 | 5/1998 |
| WO | WO-9912302 A1 | 3/1999 |
| WO | WO-03053515 A1 | 7/2003 |
| WO | WO-2005099816 A1 | 10/2005 |
| WO | WO-2005099817 A1 | 10/2005 |
| WO | WO-2006020546 A1 | 2/2006 |
| WO | WO-2006020549 A1 | 2/2006 |
| WO | WO-2006116004 A1 | 11/2006 |

OTHER PUBLICATIONS

"U.S. Appl. No. 11/733,339, Notice of Allowance mailed Feb. 25, 2010", 6 pgs.

"U.S. Appl. No. 11/733,339, Notice of Allowance mailed Apr. 21, 2010", 6 pgs.

"U.S. Appl. No. 12/102,480, Non-Final Office Action mailed Aug. 18, 2010", 9 pgs.

"European Application Serial No. 06750873.9, Office Action mailed Apr. 14, 2010", 5 pgs.

"European Application Serial No. 06750873.9, Response filed Sep. 16, 2009 to Communication mailed May 7, 2009", 7 pgs.

"U.S. Appl. No. 10/025,183, Non-Final Office Action mailed Dec. 10, 2007", 4 pgs.

"U.S. Appl. No. 10/025,183, Notice of Allowance mailed Sep. 14, 2007", 4 pgs.

"U.S. Appl. No. 10/025,223, Final Office Action mailed Aug. 16, 2004", 9 pgs.

"U.S. Appl. No. 10/025,223, Final Office Action mailed Sep. 10, 2004", 7 pgs.

"U.S. Appl. No. 10/025,223, Final Office Action mailed Aug. 16, 2004", 8 pgs.

"U.S. Appl. No. 10/025,223, Final Office Action mailed Sep. 10, 2004", 7 pgs.

"U.S. Appl. No. 10/025,223, Non Final Office Action mailed Mar. 1, 2005", 8 pgs.

"U.S. Appl. No. 10/025,223, Non Final Office Action mailed Mar. 19, 2004", 6 pgs.

"U.S. Appl. No. 10/025,223, Non-Final Office Action mailed Mar. 1, 2005", 6 pgs.

"U.S. Appl. No. 10/025,223, Non-Final Office Action mailed Mar. 19, 2004", 5 pgs.

"U.S. Appl. No. 10/025,223, Notice of Allowance mailed Aug. 10, 2005", 6 pgs.

"U.S. Appl. No. 10/025,223, Notice of Allowance mailed Aug. 10, 2005", 4 pgs.

"U.S. Appl. No. 10/025,223, Response filed Jan. 10, 2005 to Final Office Action mailed Sep. 10, 2004", 10 pgs.

"U.S. Appl. No. 10/025,223, Response filed Jun. 21, 2004 to Non Final Office Action mailed Mar. 19, 2004", 9 pgs.

"U.S. Appl. No. 10/025,223, Response filed Jun. 30, 2005 to Non Final Office Action mailed Mar. 1, 2005", 10 pgs.

"U.S. Appl. No. 10/025,223, Response filed Nov. 11, 2004 to Final Office Action mailed Aug. 16, 2004", 16 pgs.

"U.S. Appl. No. 10/071,255, Non Final Office Action mailed Jan. 7, 2005", 6 pgs.

"U.S. Appl. No. 10/071,255, Notice of allowance mailed Jun. 15, 2005", 4 pgs.

"U.S. Appl. No. 10/071,255, Preliminary Amendment filed Oct. 5, 2005", 12 pgs.

"U.S. Appl. No. 10/071,255, Response and Preliminary Amendment filed Oct. 20, 2004 to Restriction Requirement mailed Sep. 28, 2004", 10 pgs.

"U.S. Appl. No. 10/071,255, Response filed Apr. 7, 2005 Non-Final Office Action mailed Jan. 7, 2005", 12 pgs.

"U.S. Appl. No. 10/071,255, Restriction Requirement mailed Sep. 28, 2004", 5 pgs.

"U.S. Appl. No. 10/744,943, Final Office Action mailed Feb. 21, 2008", 15 pgs.

"U.S. Appl. No. 10/744,943, Response filed Oct. 22, 2007 to Non-Final Office Action Mailed Apr. 20, 2007", 9 pgs.

"U.S. Appl. No. 10/870,328, Non Final Office Action mailed Aug. 16, 2007", 12 pgs.

"U.S. Appl. No. 10/870,328, Response filed Nov. 16, 2007 to Non-Final Office Action mailed Aug. 16, 2007", 17 pgs.

"U.S. Appl. No. 10/914,496, Final Office Action mailed May 23, 2007", 11 pgs.

"U.S. Appl. No. 10/914,496, Non Final Office Action mailed Dec. 5, 2006", 9 pgs.

"U.S. Appl. No. 10/914,496, Non-Final Office Action mailed Mar. 18, 2008", 9 pgs.

"U.S. Appl. No. 10/914,496, Response filed Mar. 5, 2007 to Non Final office Action mailed Dec. 5, 2006", 13 pgs.

"U.S. Appl. No. 10/914,496, Response filed Aug. 22, 2007 to Final Office Action mailed May 23, 2007", 12 pgs.

"U.S. Appl. No. 10/914,499, Non-Final Office Action mailed May 29, 2007", 11 pgs.

"U.S. Appl. No. 10/914,499, Final Office Action mailed Jan. 24, 2008", 10 pgs.

"U.S. Appl. No. 11/039,200, Non Final office action mailed Aug. 3, 2006", 10 pgs.

"U.S. Appl. No. 11/039,200, Notice of allowance mailed Dec. 15, 2006", 4 pgs.

"U.S. Appl. No. 11/039,200, Response filed Nov. 2, 2006 to Non Final office action mailed Aug. 3, 2006", 9 pgs.

"U.S. Appl. No. 11/101,142, Non-Final Office Action mailed Jun. 20, 2007", 8 pgs.

"U.S. Appl. No. 11/101,142, Notice of Allowance mailed Nov. 27, 2007", 5 pgs.

"U.S. Appl. No. 11/101,142, Response filed Jun. 4, 2007 to Restriction Requirement Response mailed May 3, 2007", 7 pgs.

"U.S. Appl. No. 11/101,142, Response filed Sep. 20, 2007 to Non-Final Office Action mailed Jun. 20, 2007", 7 pgs.

"U.S. Appl. No. 11/101,142, Restriction Requirement mailed May 3, 2007", 5 pgs.

"U.S. Appl. No. 11/101,196, Non Final Office Action mailed Mar. 29, 2007", 8 pgs.

"U.S. Appl. No. 11/101,196, Notice of Allowance mailed Aug. 27, 2007", 5 pgs.

"U.S. Appl. No. 11/101,196, Response filed Jun. 29, 2007 to Non Final Office Action mailed Mar. 29, 2007", 8 pgs.

"U.S. Appl. No. 11/116,108, Advisory Action mailed Jan. 29, 2009", 3 pgs.

"U.S. Appl. No. 11/116,108, Non-Final Office Action mailed Mar. 20, 2008", 12 pgs.

"U.S. Appl. No. 11/116,108, Non-Final Office Action mailed Apr. 23, 2009", 7 pgs.

"U.S. Appl. No. 11/116,108, Notice of Allowance mailed Sep. 29, 2009", 10 pgs.

"U.S. Appl. No. 11/116,108, Response filed Jul. 23, 2009 to Non Final Office Action mailed Apr. 23, 2009", 7 pgs.

"U.S. Appl. No. 11/116,108, Response filed Dec. 10, 2008 to Final Office Action mailed Oct. 10, 2008", 6 pgs.

"U.S. Appl. No. 11/116,108, Response filed Jun. 20, 2008 to Non-Final Office Action mailed Mar. 20, 2008", 9 pgs.

"U.S. Appl. No. 11/325,564, Examiner Interview Summary mailed Jun. 24, 2009", 2 pgs.

"U.S. Appl. No. 11/325,584, Final Office Action mailed Oct. 24, 2008", 5 pgs.

"U.S. Appl. No. 11/325,584, Non-Final Office Action mailed Mar. 24, 2009", 5 pgs.

"U.S. Appl. No. 11/325,584, Non-Final Office Action mailed Apr. 10, 2008", 6 pgs.

"U.S. Appl. No. 11/325,584, Notice of Allowance mailed Oct. 21, 2009", 5 pgs.

"U.S. Appl. No. 11/325,584, Response filed Jan. 22, 2009 to Final Office Action mailed Oct. 24, 2008", 6 pgs.

"U.S. Appl. No. 11/325,584, Response filed Jun. 24, 2009 to Non Final Office Action maield Mar. 24, 2009", 9 pgs.

"U.S. Appl. No. 11/325,584, Response filed Jul. 10, 2008 to Non Final Office Action mailed Apr. 10, 2008", 9 pgs.

"U.S. Appl. No. 11/733,339, Non Final Office Action mailed Apr. 30, 2009", 10 pgs.

"U.S. Appl. No. 11/733,339, Non-Final Office Action mailed Sep. 9, 2009", 9 Pgs.

"U.S. Appl. No. 11/733,339, Response filed Dec. 4, 2009 to Non Final Office Action mailed Sep. 9, 2009", 11 pgs.

"U.S. Appl. No. 11/116,108, Final Office Action mailed Oct. 10, 2008", 7 pgs.

"European Application No. 06750873.9 Office Action mailed on May 7, 2009", 2 pgs.

"International Application No. PCT/US2002/040488, International Search Report mailed May 9, 2003", 7 pgs.

"International Application No. PCT/US2005/028059, International Preliminary Report on Patentability mailed Feb. 13, 2007", 9 pgs.

"International Application No. PCT/US2005/028059, International Search Report and Written Opinion mailed Jan. 12, 2005", 13 pgs.

"International Application No. PCT/US2006/014957, International Search Report and Written Opinion mailed Sep. 29, 2006", 16 pgs.

"International Application No. PCT/US2005/011639, International Search Report and Written Opinion mailed Aug. 26, 2005", 12 pgs.

"International Application No. PCT/US2005/011606, International Search Report and Written Opinion mailed Jul. 26, 2005", 12 pgs.

"International Application No. PCT/US2007/069424, International Search Report mailed Dec. 27, 2007", 4 pgs.

"International Application No. PCT/US2007/069424, Written Opinion mailed Dec. 27, 2007", 9 pgs.

"International Application No. PCT/US2007/069426, International Search Report mailed Dec. 27, 2007", 4 pgs.

"International Application No. PCT/US2007/069426, Written Opinion mailed Dec. 27, 2007", 8 pgs.

Adams, J. T, "An introduction to IEEE STD 802.15.4", *2006 IEEE Aerospace Conference*, Big Sky, MT, (2006), 1-8.

Bange, Joseph E, et al., "Implantable Medical Device Telemetry With Adaptive Frequency Hopping", U.S. Appl. No. 11/456,937, filed Jul. 12, 2006, 35 pgs.

Bange, Joseph E, et al., "Implantable Medical Device Telemetry With Periodic Frequency Hopping", U.S. Appl. No. 11/456,942, filed Jul. 12, 2006, 43 pgs.

Bange, Joseph E, et al., "System and Method for RF Transceiver Duty Cycling in an Implantable Medical Device", U.S. Appl. No. 11/101,196, filed Apr. 7, 2005, 19 pgs.

Bange, Joseph E, et al., "System and Method for RF Wake-Up of Implantable Medical Device", U.S. Appl. No. 11/101,142, filed Apr. 7, 2005, 19 pgs.

Duflot, M., et al., "A formal analysis of bluetooth device discovery", *International Journal on Software Tools for Technology Transfer (STTT)*, 8(6), (Jul. 2006), 621-632.

Golmie, N., et al., "The Evolution of Wireless LANs and PANs—Bluetooth and WLAN coexistence: challenges and solutions", *IEEE Personal Communications*, 10(6), (Dec. 2003), 22-29.

Healy, S. J., et al., "System and Method for Providing Secure Exchange of Sensitive Information With an Implantable Medical Device", U.S. Appl. No. 10/801,150, filed Mar. 15, 2004, 30 pgs.

Katoozi, M., et al., "On-Demand Retransmission of Data With an Implantable Medical Device", U.S. Appl. No. 10/870,328, filed Jun. 17, 2004, 30 pgs.

Quiles, S., "Telemetry Switchover State Machine With Firmware Priority Control", U.S. Appl. No. 10/914,499, filed Aug. 9, 2004, 30 pgs.

Quiles, Sylvia, "Automatic Power Control for a Radio Frequency Transceiver of an Implantable Device", U.S. Appl. No. 10/914,496, filed Aug. 9, 2004, 23 pgs.

Rawat, Prashant, et al., "Radio Frequency Antenna in a Header of an Implantable Medical Device", U.S. Appl. No. 10/744,943, filed Dec. 22, 2003, 34 pgs.

Seeberger, M., "Dynamic Telemetry Link Selection for an Implantable Device", U.S. Appl. No. 10/914,638, filed Aug. 9, 2004, 35 pgs.

Von Arx, J. A., et al., "A Telemetry Duty Cycle Management System for an Implantable Medical Device", U.S. Appl. No. 11/325,584, filed Jan. 4, 2006, 37 pgs.

Von Arx, Jeffrey, "Dynamic Telemetry Encoding for an Implantable Medical Device", U.S. Appl. No. 10/870,324, filed Jun. 17, 2004, 38 pgs.

Zhu, H., et al., "A survey of quality of service in IEEE 802.11 Networks", *IEEE Wireless Communications*, IEEE Service Center, Piscataway, NJ, US, 11(4), (Aug. 2004), 6-14 pgs.

\* cited by examiner

SYSTEM AND METHOD FOR ENABLING COMMUNICATIONS WITH IMPLANTABLE MEDICAL DEVICES

CROSS REFERENCE TO RELATED APPLICATIONS

This application is a Division of U.S. application Ser. No. 11/116,108, filed on Apr. 27, 2005, now issued as U.S. Pat. No. 7,664,553, which is incorporated herein by reference in its entirety.

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices (IMDs), including cardiac rhythm management devices such as pacemakers and implantable cardioverter/defibrillators, typically have the capability to communicate data with an external device (ED) via a radio-frequency telemetry link. One such external device is an external programmer used to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

External programmers are commonly configured to communicate with an IMD over an inductive link. Coil antennas in the external programmer and the IMD are inductively coupled so that data can be transmitted by modulating a carrier waveform which corresponds to the resonant frequency of the two coupled coils. An inductive link is a short-range communications channel requiring that the coil antenna of the external device be in close proximity to the IMD, typically within a few inches. Other types of telemetry systems may utilize far-field radio-frequency (RF) electromagnetic radiation to enable communications between an IMD and an ED over a wireless medium. Such long-range RF telemetry allows the IMD to communicate with an ED, such as an external programmer or remote monitor, without the need for close proximity.

In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. Active transmitters and receivers for this frequency range require special RF components (typically including SiGe or GaAs semiconductor devices) that consume a significant amount of power (typically tens of milliwatts). Implantable medical devices, however, are powered by a battery contained within the housing of the device that can only supply a limited amount of continuous power before it fails. When the battery fails in an implantable device, it must be replaced which necessitates a re-implantation procedure. Power conservation is thus an important design objective in wireless telemetry systems for implantable medical devices.

It is also common in clinical settings for there to be multiple implantable and/or external devices present in an area so that communication over the wireless medium is possible between the multiple devices. Access to the medium among the multiple devices must be controlled in this situation in order for a communications session between any pair of devices to be established. It would also be desirable for there to be the possibility of multiple communications sessions between different devices occurring concurrently. Providing a means by which communications may be rapidly established with an IMD in this environment within the constraints imposed by power conservation considerations, however, is problematic. Also, in either the home or the clinic, there are external sources of RF energy which may interfere with communication between the ED and IMD, and this problem must also be dealt with.

SUMMARY

The present invention relates to a telemetry system for enabling radio-frequency (RF) communications between an implantable medical device and an external device in a multiple device environment in a manner which reduces the power requirements of the implantable devices. Each of the implantable devices is programmed to power up its transmitter and receiver for a specified time window at periodic intervals defined by the wakeup timer and wait for receipt of special wakeup characters transmitted by the external device. In order to wakeup and establish communications with only one selected implantable device among a plurality of such devices that are within range, an identification code unique to a particular implantable device is also transmitted by the external device. If the implantable device determines that its identification code has been transmitted, it then transmits an acknowledge signal and waits a specified period of time for a response from the external device. The external device and the implantable device then attempt to establish a communications session when a response to the acknowledge signal is received by the implantable device. Multiple communications channels separated in frequency may be used for narrow-band noise avoidance and to enable simultaneous communications sessions between devices. One or more of the multiple communications channels may be dedicated for use as control channels in transmitting the wakeup sequence and establishing a communications session.

DETAILED DESCRIPTION

Figure 1:
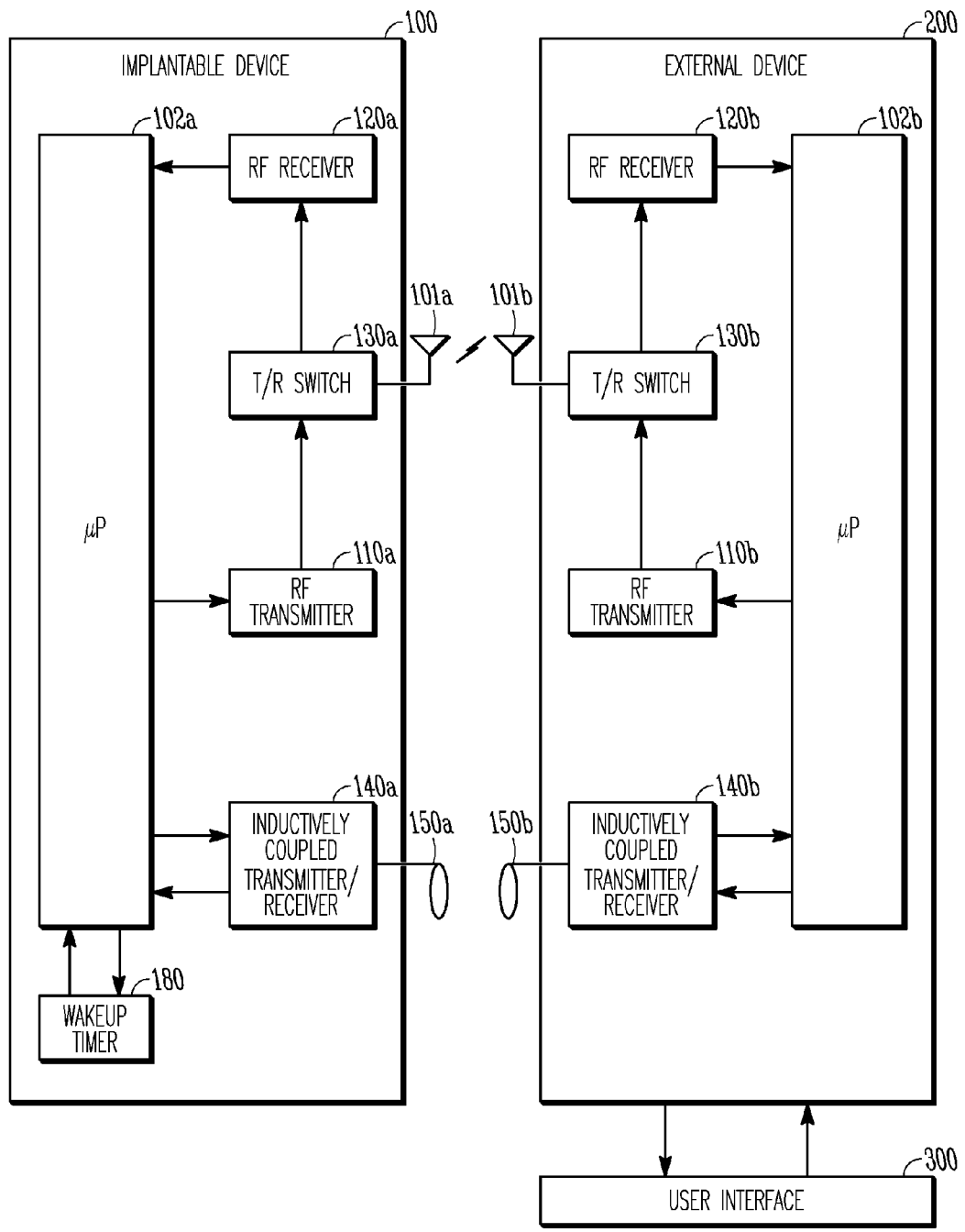
FIG. 1 is a block diagram of a telemetry system for an implantable device and an external device.

Power consumption by an implantable device may be lessened by managing the duty cycle of the RF transmitting and receiving components. Long-range RF telemetry circuitry (i.e., the transmitter and receiver) typically requires power on the order of tens of milliwatts in order to operate. Implantable cardiac devices in use today, on the other hand, are usually designed to operate with average power in the microwatt range. This means that the RF telemetry circuitry must be duty cycled down in order to meet the power budget of such devices. The RF telemetry circuitry of an implantable device can either be powered up or down, referred to as awake and sleep states, respectively. Duty cycling of the implantable device's RF telemetry circuitry can be implemented by a wakeup timer which defines periodic wakeup intervals at which the implantable device powers up its RF circuitry and listens for a transmission from an external device for a specified period of time, referred to as a wakeup window. Upon acknowledging the transmission from the external device, a communications session can be established by a handshaking protocol, and data can then be transferred between the devices. In order to minimize power consumption, it is desirable for the RF circuitry of the implantable device to be powered up for as short a time as possible at each wakeup interval while still being able to reliably recognize session requests from the external device. If the implantable device recognizes a session request from the external device during its wakeup window, it remains awake long enough to establish a communications session with the external device; otherwise, the implantable device returns to a sleep state until the next wakeup interval occurs.

Described herein is a telemetry system for enabling radio-frequency (RF) communications between an implantable medical device and an external device in a multiple device environment in a manner which reduces the power requirements of the implantable device. In an exemplary system, the external device is programmed to transmit a data segment containing a repeating sequence of special wakeup characters in order to establish a communications session with the implantable device. The implantable device is programmed to power up its transmitter and receiver for a specified time window, referred to as a wakeup window, at periodic wakeup intervals defined by the wakeup timer and wait for receipt of one of the special wakeup characters transmitted by the external device. The implantable device maintains its transmitter and receiver in a powered-up state upon receipt of a special character and for as long as consecutive special wakeup characters continue to be received. In order to wakeup and establish communications with only one selected implantable device among a plurality of such devices that are within range, an identification code unique to a particular implantable device is also transmitted by the external device. In one embodiment, the identification code is included in the wakeup sequence so that a unique wakeup sequence is used to wakeup each implantable device. In another embodiment, the identification code is transmitted after one or more wakeup characters are transmitted. Once an implantable device is woken up by the wakeup characters, the device continues to receive data until it determines whether or not its identification code has been transmitted. If the implantable device determines that its identification code has been transmitted, it then transmits an acknowledge signal and waits a specified period of time for a response from the external device. When a response to the acknowledge signal is received by the implantable device, the external device and the implantable device are programmed to establish a communications session by a handshaking protocol. During a communications session, the RF transmitter and receiver of the implantable device may then either be maintained in the powered-up state for the duration of the communications session or powered down at prescribed intervals according to a defined protocol.

The controllers of the external and implantable devices may be programmed to operate their respective telemetry hardware in a manner which utilizes multiple communications channels. The multiple channels are defined with different carrier frequencies so that communications over one channel does not disturb communications over any of the other channels. By using multiple channels for data transfer, a plurality of communications sessions with different implantable devices may take place simultaneously. Also, most noise from external sources is of the narrow-band type, where the energy of the noise is confined to a particular frequency range. Examples of narrow-band noise sources include communications devices such as wireless telephones as well as many other kinds of electronic equipment which are commonly found in the home and in the clinic. When such narrow-band noise is in the same frequency range used for telemetry, it is said to be in-band and can interfere with communications between the devices. The use of multiple communications channels helps to alleviate this problem since, at any given time, only the channels at the same frequency as the in-band noise are interfered with. The devices may be programmed to test a channel for both noise and the presence of other traffic before using that channel for communications.

The wakeup scheme described above, however, requires the external device to use a channel for transmitting the wakeup sequence that is expected by the implantable device. A channel may therefore be dedicated to use for waking up and establishing communications with an implantable device, referred to as a wakeup channel or control channel, with the other channels used for data communications referred to as data channels. Once a communications session is established, the external device finds an available and non-noisy data channel and transmits the information to the implantable device so that both devices can switch to that channel for data transfer. The control channel is then freed up for use by other devices in establishing communications sessions. In another embodiment, multiple control channels are employed in order to allow for the possibility that narrow-band noise could render a single control channel unusable. The implantable device in that case may be programmed to power up its receiver and listen for wakeup characters on the different control channels. The wakeup intervals for the different control channels could be the same or different.

1. Exemplary Hardware Components

FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that includes a microprocessor and memory for data and program storage that supervises overall device operation as well as telemetry. Code executed by the controller also implements the duty cycle management schemes to be described below. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) enables a user such as a clinician to direct the operation of the external device.

A long-range RF receiver 120a or 120b and a long-range RF transmitter 110a or 110b are interfaced to the microprocessor 102a or 102b in the implantable device and the external device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver. To effect communications between the devices, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The implantable device also incorporates a means by which the controller can power up or power down the RF receiver and/or transmitter in order to manage duty cycles in the manner described below. A wakeup timer 180 for defining the RF duty cycle is also shown for the implantable device, and this timer can either be implemented in code executed by the controller or can be discrete components. FIG. 1 also shows an inductively coupled transmitter/receiver 140a or 140b and antenna 150a or 150b for the implantable and external devices by which communication may take place without concern for power consumption when the two devices are in close physical proximity to one another.

2. Description of Communications Enablement Scheme

Figure 2:
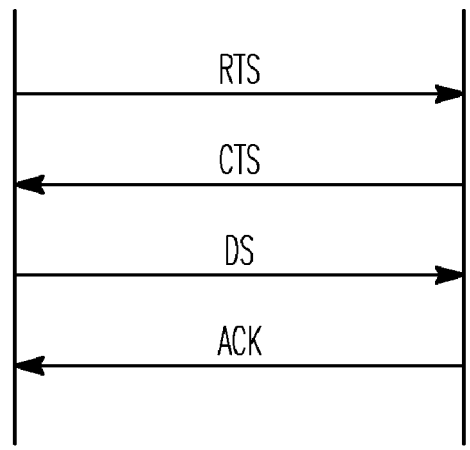
FIG. 2 illustrates a handshaking protocol for collision avoidance.

A wireless telemetry system for implantable medical devices is generally a multiple access network in which a number of network participants share the available bandwidth of the wireless medium. A medium access control (MAC) protocol may be defined which allows each network participant to acquire exclusive access to the medium before transmitting data to an intended recipient. A collision is said to occur when two or more participants attempt to transmit at the same time. In certain networks, collisions may be detected by the sender listening to the medium when a transmission is initiated to determine if other network activity is present. If a collision is detected, the sender ceases transmitting and waits for a random or defined period before trying again. Most wireless transceivers operate in a half-duplex mode, however, and cannot simultaneously transmit and listen for ongoing network activity. MAC protocols for wireless networks therefore typically use out-of-band signaling or a handshaking protocol to minimize the probability of a collision occurring. In an example of the latter type of protocol, a four-way RTS-CTS-DS-ACK exchange as illustrated by FIG. 2 is used to avoid collisions. A network participant who desires to send a message to a particular recipient first transmits a request-to-send (RTS) frame and waits a defined period of time for a clear-to-send (CTS) frame from the intended recipient. All other network participants who hear either of the RTS or CTS frames defer their transmissions. Upon receiving the CTS response, the sender can assume that the medium has been exclusively acquired and can then begin transmission of a data segment (DS) to the recipient. If the data is received without errors, the recipient responds with an acknowledge (ACK) frame which frees the medium for access by another participant. The present invention, in various embodiments, may work in the context of any of the medium access control protocols discussed above.

Figure 3:
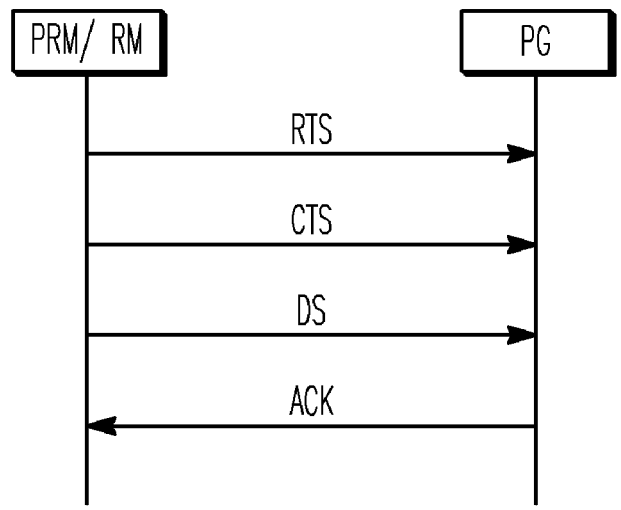
FIG. 3 illustrates a wakeup scheme in accordance with the invention.

A particular communications enablement scheme will now be described with reference to an external programmer or remote monitor (PRM/RM) and an implantable device (referred to as a pulse generator or PG). In this embodiment, the wakeup process works within the framework of a handshaking collision avoidance protocol as described above. In such a protocol, the PRM/RM transmits the RTS and CTS frames to cause other participants to defer their transmissions. It then transmits a data segment DS containing wakeup characters and a device ID to the particular PG it wants to communicate with. The awakened PG then transmits an ACK frame to release the medium. The wakeup process is illustrated by FIG. 3. The length of the DS message is set to a large number (e.g., 256 bytes), and contains a repeating sequence of a special n-bit (e.g., 10-bit) character reserved solely for use as a wakeup indicator. In one embodiment, the implantable device and the external device communicate by a transmission code which provides a DC balanced data stream such as 8b/10b. Such bit balanced data streams are advantageous in RF communications. In order for the special wakeup character to be invariant, the special wakeup character may be selected as a bit balanced sequence which is not changed by the transmission code.

The data segment also contains a device ID which may be either incorporated into the wakeup indicator itself by employing unique wakeup characters for each PG or may be a separate sub-segment transmitted after the wakeup characters. The PG wakes up periodically (e.g., every 20-30 seconds) and listens for a very short interval to receive a wakeup special character. If one wakeup special character is received, then the PG will stay awake long enough to receive several more wakeup special characters. In one embodiment, the wakeup characters are unique to the PG, and the awakened PG knows that the PRM/RM wants to establish a communications session with it. The PG then remains awake after the data segment is finished and transmits an ACK frame to the PRM/RM. In another embodiment, the awakened PG waits for a device ID which occurs later in the data segment, and it goes back to a sleep state if the device ID does not match its own. Otherwise, the PG remains awake after the data segment and responds with an ACK frame. After transmitting the ACK frame, the PG then stays awake for an extended period of time in order to receive a response from the PRM/RM. The PRM having successfully received this ACK message proceeds to perform a connection process which will contend for message traffic within the protocol framework in order to establish a communications session with the PG.

Figure 4:
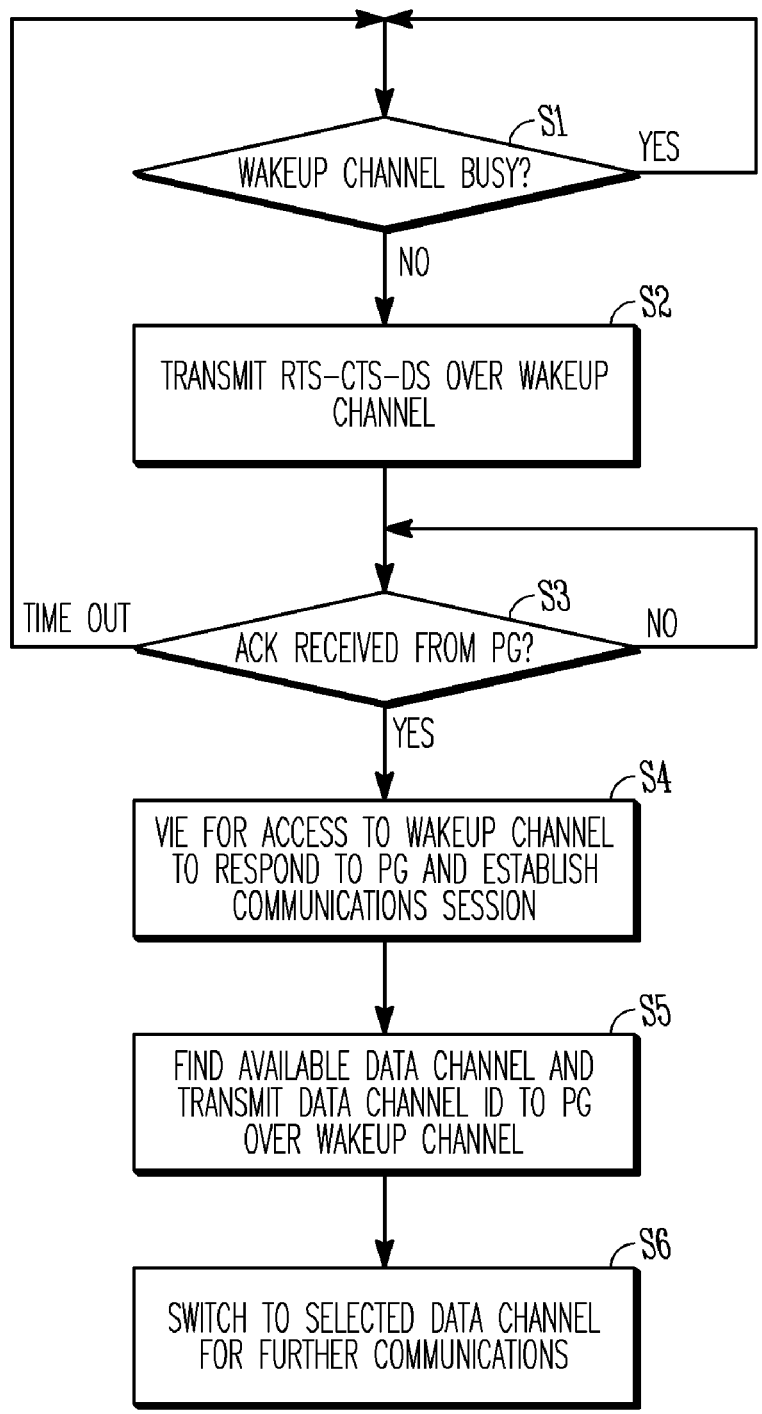
FIG. 4 illustrates the steps performed by the PRM/RM in establishing a communications session in the multiple channel environment.

The communications scheme just described enables a PRM/RM to establish a communications session with a selected one among a plurality of PG's using a single communications channel which is shared among the PG's. In further modification, the communications system utilizes multiple communications channels separated in frequency. One of the channels is dedicated for use as a control or wakeup channel with the other channels used as data channels for continuing communications sessions established over the wakeup channel. FIG. 4 illustrates the steps performed by the PRM/RM in establishing a communications session in the multiple channel environment. The PG's are configured to periodically wake up and listen for wakeup characters on the wakeup channel in the manner described above. At step S1, the PRM/RM waits until it determines that the wakeup channel is available (e.g., by receiving an ACK frame from some other device on the channel or by determining that there is no traffic on the channel). At step S2, it transmits the RTS-CTS-DS sequence over the wakeup channel, where the DS frame includes the device ID of the PG it wants to communicate with as described above. At step S3, the PRM/RM waits for an ACK from the PG. If no ACK is received after a specified period of time, a time out is declared and the device returns to step S1 to transmit another wakeup sequence. Otherwise, after receiving the ACK frame, the PRM/RM at step S4 vies for access to the wakeup channel in order to respond to the PG and establish a communications session. At step S5, the PRM/RM then finds an available data channel and transmits the data channel ID to the PG over wakeup channel. At step S6, the PRM/RM and PG both switch to the selected data channel for further communications.

By having multiple data channels, the system allows data communications to take place in the event narrow-band noise renders one of the channels unusable. It may also be desirable to use multiple wakeup channels so that communications sessions can be initiated with a PG in the event that narrow-band noise corrupts one of the wakeup channels. In this embodiment, the PG may be programmed to wake up and listen for wakeup characters on each of the wakeup channels. The wakeup intervals at which the PG wakes up and listens on each of the wakeup channels may be the same or different. For example, the PG may wakeup every minute to listen for wakeup characters on a primary wakeup channel and wakeup every three minutes to listen on a secondary wakeup channel. The PRM/RM would then be programmed to transmit the wakeup sequence on the primary and secondary wakeup channels either alternately or simultaneously.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method by which an external device communicates with an implantable medical device, comprising:
   transmitting a data segment containing a repeating sequence of special wakeup characters and a device ID from the external device in order to establish a communications session with the implantable device, wherein a transmitter and receiver of the implantable device are powered up, according to a timed duty cycle, for a specified time window at periodic intervals and waits for receipt of one of the special wakeup characters transmitted by the external device;
   wherein the implantable device suspends operation of the timed duty cycle and time window, maintains the transmitter and receiver in a powered-up state upon receipt of a special character prior to receipt of the device ID and prior to establishment of a communications session and for as long as consecutive special wakeup characters continue to be received, transmits an acknowledge signal to the external device if the device ID matches an ID of the implantable device, and then waits a specified period of time for a response from the external device; and,
   establishing the communications session when a response to the acknowledge signal is received by the implantable device.

2. The method of claim 1 wherein the device ID is incorporated into the wakeup characters by using unique wakeup characters for a particular implantable device.

3. The method of claim 1 wherein the device ID is included in the data segment after the wakeup characters.

4. The method of claim 1 wherein the RF transmitter and receiver of the external and implantable devices may be switched among multiple communications channels separated in frequency.

5. The method of claim 4 including dedicating one of the multiple channels for use as a wakeup channel for establishing a communications session and using the remaining channels for data channels for continuing established communications sessions.

6. The method of claim 5 wherein the external device transmits an RTS frame, a CTS frame, and the data segment over the wakeup channel, the implantable device responds by transmitting an ACK frame over the wakeup channel.

7. The method of claim 6 wherein the external device, after receiving the ACK frame from the external device over the wakeup channel, vies for access to the wakeup channel in order to respond to the implantable device and establish a communications session.

8. The method of claim 7 wherein the external device, after establishing a communications session with the implantable device, finds an available data channel, transmits an ID of the data channel to the implantable device over wakeup channel, and switches to the selected data channel for further communications.

9. The method of claim 1 wherein the implantable device and the external device communicate by a transmission code which provides a DC balanced data stream.

10. The method of claim 9 where the transmission code is 8b/10b.

11. The method of claim 1 wherein the device ID is unique to the implantable medical device.

12. The method of claim 5 wherein transmitting a data segment includes transmitting the data segment when the external device detects no activity on the dedicated wakeup channel.

13. The method of claim 5 wherein transmitting a data segment includes transmitting the data segment when the external device receives an ACK frame via the dedicated wakeup channel.

14. The method of claim 5 wherein dedicating one of the multiple channels for use as a wakeup channel includes dedicating a plurality of the multiple channels for use as wakeup channels and using the remaining channels for data channels, and wherein powering the receiver of the implantable medical device includes powering the receiver of the implantable medical device for a specified time window at a different periodic interval for each of the wakeup channels.

15. The method of claim 1 wherein transmitting a data segment containing a repeating sequence of special wakeup characters and a device ID from the external device includes transmitting a data segment containing a repeating n-bit wakeup indicator over M bytes of the data segment where n and M are integers.

16. The method of claim 1 including transmitting from the external device both a request for access to a communication medium and a response to the request in order to access the communication medium.

17. An implantable medical device comprising:
   an antenna, an RF transmitter, an RF receiver, a controller, and a wakeup timer, wherein the controller is interfaced to the transmitter and receiver and configured to:
      enable the transmitter and receiver to be powered up and down;
      operate the transmitter and receiver according to a timed duty cycle that powers up the transmitter and receiver for a specified time window at periodic intervals defined by the wakeup timer to wait for receipt of a special wakeup character repeated in a data segment and a device ID transmitted by an external device;
      suspend operation of the timed duty cycle and wakeup timer, and maintain the transmitter and receiver in a powered-up state upon receipt of the special wakeup character prior to receipt of the device ID and prior to establishment of a communications session and for as long as consecutive special wakeup characters continue to be received;

transmit an acknowledge signal to establish a communications session when the received device ID matches an ID of the implantable device; and wait a specified period of time for a response to the acknowledge signal.

18. The implantable medical device of claim 17 wherein the transmitter and receiver are configured to transmit and receive a wireless signal via multiple communications channels separated in frequency.

19. The implantable medical device of claim 18 wherein the receiver is configured to receive the special wakeup character via a communication channel dedicated as a wakeup channel for establishing the communications session and to use the other channels of the multiple communication channels as data channels.

20. The implantable medical device of claim 17 wherein the special wakeup character is a repeating n-bit wakeup indicator and the device ID is unique to the implantable medical device.

* * * * *

Disclaimer

8,055,350 B2—Earle Roberts, Maple Grove, MN (US). SYSTEM AND METHOD FOR ENABLING COMMUNICATIONS WITH IMPLANTABLE MEDICAL DEVICES. Patent dated November 8, 2011. Disclaimer filed December 12, 2011, by the assignee, Cardiac Pacemakers, Inc.

The term of this patent shall not extend beyond the expiration date of patent numbers 8,024,043 and 7,359,753.

*(Official Gazette, February 21, 2012)*